(12) United States Patent
Kelly et al.

(10) Patent No.: US 6,350,763 B1
(45) Date of Patent: Feb. 26, 2002

(54) SMALL MOLECULES USEFUL IN THE TREATMENT OF INFLAMMATION DISEASE

(75) Inventors: Terence Alfred Kelly, Ridgefield; Ronald John Sorcek, Bethel, both of CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 09/604,899

(22) Filed: Jun. 28, 2000

Related U.S. Application Data
(60) Provisional application No. 60/144,844, filed on Jul. 21, 1999.

(51) Int. Cl.$^7$ .................. A61K 31/44; C07D 401/00
(52) U.S. Cl. .................... 514/341; 546/274.4
(58) Field of Search ............ 546/274.1, 274.4; 514/341

(56) References Cited

FOREIGN PATENT DOCUMENTS

| EP | 91596 | * | 10/1983 |
| EP | 770613 | * | 5/1997 |
| FR | 2597865 | * | 5/1997 |

OTHER PUBLICATIONS

Kwiatkowski et al., "Use of molecular electrostatic potentials for analysis of anticonvulsant activities of phenylsuccinimides", SAR QSAR Environ. Res., 1(2–3), 233–44, 1993.*

* cited by examiner

Primary Examiner—Alan L. Rotman
Assistant Examiner—Binta Robinson
(74) Attorney, Agent, or Firm—Robert P. Raymond; Alan R. Stempel; Mary-Ellen M. Devlin

(57) ABSTRACT

Novel compounds of the formula I

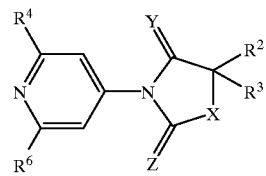

(I)

which are useful for treating or preventing inflammatory and immune cell-mediated diseases. Exemplary compounds are:

1-acetyl-5-(R)-(4-bromobenzyl)-3-(2,6-dichloropyridin-4-yl)-5-methylimidazoline-2,4-dione;

5-(R)-(4-bromobenzyl)-3-(2,6-dichloropyridin-4-yl)-1-ethyl-5-methylimidazoline-2,4-dione; and, 5-(R)-(4-bromobenzyl)-3-(2,6-dichloropyridin-4-yl)-5-methylimidazoline-2,4-dione.

6 Claims, No Drawings

SMALL MOLECULES USEFUL IN THE TREATMENT OF INFLAMMATION DISEASE

RELATED APPLICATIONS

The benefit of prior provisional application Ser. No. 60/144,844, filed on Jul. 21, 1999, is hereby claimed.

FIELD OF THE INVENTION

The present invention relates generally to a series of novel small molecules, their synthesis and their use in the treatment of inflammatory disease.

BACKGROUND OF THE INVENTION

Research spanning the last decade has helped to elucidate the molecular events attending cell-cell interactions in the body, especially those events involved in the movement and activation of cells in the immune system. See generally, Springer, T. *Nature*, 1990, 346, 425–434. Cell surface proteins, and especially the Cellular Adhesion Molecules ("CAMs") and "Leukointegrins", including LFA-1, MAC-1 and gp150.95 (referred to in WHO nomenclature as CD18/CD11a, CD18/CD11b, and CD18/CD11c, respectively) have correspondingly been the subject of pharmaceutical research and development having as its goal the intervention in the processes of leukocyte extravasation to sites of injury and leukocyte movement to distinct targets. For example, it is presently believed that prior to the leukocyte extravasation, which is a mandatory component of the inflammatory response, activation of integrins constitutively expressed on leukocytes occurs and is followed by a tight ligand/receptor interaction between integrins (e.g., LFA-1) and one or several distinct intercellular adhesion molecules (ICAMs) designated ICAM-1, ICAM-2, ICAM-3 or ICAM-4 which are expressed on blood vessel endothelial cell surfaces and on other leukocytes. The interaction of the CAMs with the Leukointegrins is a vital step in the normal functioning of the immune system. Immune processes such as antigen presentation, T-cell mediated cytotoxicity and leukocyte extravasation all require cellular adhesion mediated by ICAMs interacting with the Leukointegrins. See generally Kishimoto, T. K.; Rothlein; R. R. *Adv. Pharmacol.* 1994, 25, 117–138 and Diamond, M.; Springer, T. *Current Biology*, 1994, 4, 506–532.

A group of individuals has been identified which lack the appropriate expression of Leukointegrins, a condition termed "Leukocyte Adhesion Deficiency" (Anderson, D. C.; et al., *Fed. Proc.* 1985, 44, 2671–2677 and Anderson, D. C.; et al., *J. Infect. Dis.* 1985, 152, 668–689). These individuals are unable to mount a normal inflammatory and/or immune response(s) due to an inability of their cells to adhere to cellular substrates. These data show that immune reactions are mitigated when lymphocytes are unable to adhere in a normal fashion due to the lack of functional adhesion molecules of the CD18 family. By virtue of the fact that LAD patients who lack CD18 cannot mount an inflammatory response, it is believed that antagonism of CD18, CD11/ICAM interactions will also inhibit an inflammatory response.

It has been demonstrated that the antagonism of the interaction between the CAMs and the Leukointegrins can be realized by agents directed against either component. Specifically, blocking of the CAMs, such as for example ICAM-1, or the Leukointegrins, such as for example LFA-1, by antibodies directed against either or both of these molecules effectively inhibits inflammatory responses. In vitro models of inflammation and immune response inhibited by antibodies to CAMs or Leukointegrins include antigen or mitogen-induced lymphocyte proliferation, homotypic aggregation of lymphocytes, T-cell mediated cytolysis and antigen-specific induced tolerance. The relevance of the in vitro studies are supported by in vivo studies with antibodies directed against ICAM-1 or LFA-1. For example, antibodies directed against LFA-1 can prevent thyroid graft rejection and prolong heart allograft survival in mice (Gorski, A.; *Immunology Today*, 1994, 15, 251–255). Of greater significance, antibodies directed against ICAM-1 have shown efficacy in vivo as anti-inflammatory agents in human diseases such as renal allograft rejection and rheumatoid arthritis (Rothlein, R. R.; Scharschmidt, L., in: *Adhesion Molecules*; Wegner, C. D., Ed.; 1994, 1–38, Cosimi, C. B.; et al., *J. Immunol.* 1990, 144, 4604–4612 and Kavanaugh, A.; et al., *Arthritis Rheum.* 1994, 37, 992–1004) and antibodies directed against LFA-1 have demonstrated immunosuppressive effects in bone marrow transplantation and in the prevention of early rejection of renal allografts (Fischer, A.; et al., *Lancet*, 1989, 2, 1058–1060 and Le Mauff, B.; et al., *Transplantation*, 1991, 52, 291–295).

It has also been demonstrated that a recombinant soluble form of ICAM-1 can act as an nhibitor of the ICAM-1 interaction with LFA-1. Soluble ICAM-1 acts as a direct ntagonist of CD18,CD11/ICAM-1 interactions on cells and shows inhibitory activity in in vitro models of immune response such as the human mixed lymphocyte response, cytotoxic T cell responses and T cell proliferation from diabetic patients in response to islet cells (Becker, J. C.; et al., *J. Immunol.* 1993, 151, 7224 and Roep, B. O.; et al., *Lancet*, 1994, 343, 1590).

Thus, the prior art has demonstrated that large protein molecules which antagonize the binding of the CAMs to the Leukointegrins have therapeutic potential in mitigating inflammatory and immunological responses often associated with the pathogenesis of many autoimmune or inflammatory diseases. However proteins have significant deficiencies as therapeutic agents, including the inability to be delivered orally and potential immunoreactivity which limits the utility of theses molecules for chronic administration. Furthermore, protein-based therapeutics are generally expensive to produce.

Several small molecules have been described in the literature which affect the interaction of CAMs and Leukointegrins. A natural product isolated from the root of *Trichilia rubra* was found to be inhibitory in an in vitro cell binding assay (Musza, L. L.; et al., *Tetrahedron*, 1994, 50, 11369–11378). One series of molecules (Boschelli, D. H.; et al., *J. Med. Chem.* 1994, 37, 717 and Boschelli, D. H.; et al., *J. Med. Chem.* 1995, 38, 4597–4614) was found to be orally active in a reverse passive Arthus reaction, an induced model of inflammation that is characterized by neutrophil accumulation (Chang, Y. H.; et al., *Eur. J. Pharmacol.* 1992, 69, 155–164). Another series of molecules was also found to be orally active in a delayed type hypersensitivity reaction in rats (Sanfilippo, P. J.; et al., *J. Med. Chem.* 1995, 38, 1057–1059). All of these molecules appear to act nonspecifically, either by inhibiting the transcription of ICAM-1 along with other proteins or act intracellularly to inhibit the activation of the Leukointegrins by an unknown mechanism. None of the molecules directly antagonize the interaction of the CAMs with the Leukointegrins. Due to lack of potency, lack of selectivity and lack of a specific mechanism of action, the described small molecules are not likely to be satisfactory for therapeutic use.

It follows that small molecules having the similar ability as large protein molecules to directly and selectively antagonize the binding of the CAMs to the Leukointegrins would make preferable therapeutic agents. WO9839303 discloses a class of small molecule inhibitors of the interaction of LFA-1 and ICAM-1. WO9911258 discloses that the fungal metabolite mevinolin and derivatives bind to LFA-1 and disrupt the interaction of LFA-1 and ICAM-1.

SUMMARY OF THE INVENTION

A first aspect of the invention comprises a method for treating or preventing inflammatory and immune cell-mediated diseases by the administration of certain novel small molecules. These compounds act by inhibiting the interaction of cellular adhesion molecules, specifically by antagonizing the binding of human intercellular adhesion molecules (including ICAM-1, ICAM-2 and ICAM-3) to the Leukointegrins (especially CD18/CD11a). A second aspect of the invention comprises novel small molecules having the above-noted therapeutic activities. A third aspect of the invention comprises methods for making these novel compounds. A final aspect of the invention comprises pharmaceutical compositions comprising the above-mentioned compounds suitable for the prevention or treatment of inflammatory and immune cell-mediated conditions.

DETAILED DESCRIPTION OF THE INVENTION

The invention comprises compounds of the formula I

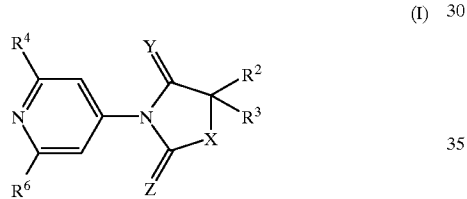

(I)

wherein:

Y is an oxygen or sulfur atom;

Z is an oxygen or sulfur atom;

X is a divalent group of the formula >CHR$^1$, >NR$^1$, >CHSO$_2$R$^1$, or >NSO$_2$R$^1$, or an oxygen or sulfur atom, wherein R$^1$ is:
  (A) a hydrogen atom,
  (B) branched or unbranched alkyl of 1 to 6 carbon atoms or cycloalkyl of 3 to 6 carbon atoms, which alkyl or cycloakyl group may be mono- or polysubstituted with:
    (i) halogen,
    (ii) oxo,
    (iii) aryl, which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more hydrogen atoms of said aryl group may be optionally and independently replaced with:
      (a) alkyl of 1 to 3 carbon atoms,
      (b) —COOH,
      (c) —SO$_2$OH,
      (d) —PO(OH)$_2$,
      (e) a group of the formula —COOR$^7$, wherein R$^7$ is straight or branched alkyl of 1 to 5 carbon atoms or cycloalkyl of 3 to 5 carbon atoms,
      (f) a group of the formula —NR$^8$R$^9$, wherein R$^8$ and R$^9$ are each independently a hydrogen atom, alkyl of 1 to 6 carbon atoms, cycloalkyl of 3 to 6 carbon atoms or acyl of 1 to 7 carbon atoms, or wherein R$^8$ and R$^9$ constitute a saturated hydrocarbon bridge of 3 to 5 carbon atoms which together with the nitrogen atom between them form a heterocyclic ring,
      (g) a group of the formula —CONR$^{10}$R$^{11}$, wherein R$^{10}$ and R$^{11}$ are each independently a hydrogen atom, alkyl of 1 to 6 carbon atoms or cycloalkyl of 3 to 6 carbon atoms, or wherein R$^{10}$ and R$^{11}$ constitute a saturated hydrocarbon bridge of 3 to 5 carbon atoms which together with the nitrogen atom between them form a heterocyclic ring,
      (h) a group of the formula —OR$^{12a}$, wherein R$^{12a}$ is a hydrogen atom, or an alkyl or acyl group of 1 to 7 carbon atoms,
      (i) a group of the formula —SR$^{12b}$, wherein R$^{12b}$ is a hydrogen atom, or an alkyl or acyl group of 1 to 7 carbon atoms,
      (j) cyano, or
      (k) an amidino group of the formula

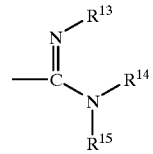

wherein R$^{13}$, R$^{14}$ and R$^{15}$ are each, independently, a hydrogen atom or alkyl of 1 to 3 carbon atoms and wherein two of R$^{13}$, R$^{14}$ and R$^{15}$ may additionally constitute a saturated hydrocarbon bridge of 3 to 5 carbon atoms which together with the nitrogen atom(s) between them form a heterocyclic ring,
    (iv) a group of the formula —COOR$^{16}$, wherein R$^{16}$ is straight or branched alkyl of 1 to 7 carbon atoms or cycloalkyl of 3 to 6 carbon atoms,
    (v) cyano,
    (vi) a group of the formula —CONR$^{17}$R$^{18}$, wherein R$^{17}$ and R$^{18}$ are each, independently, a hydrogen atom, alkyl of 1 to 6 carbon atoms or cycloalkyl of 3 to 6 carbon atoms, or wherein R$^{17}$ and R$^{18}$ constitute a saturated hydrocarbon bridge of 3 to 5 carbon atoms which together with the nitrogen atom between them form a heterocyclic ring,
    (vii) a group of the formula —OR$^{19}$, wherein R$^{19}$ is a hydrogen atom, or an alkyl or acyl group of 1 to 7 carbon atoms,
    (viii) a group of the formula —SR$^{20}$, wherein R$^{20}$ is a hydrogen atom, or an alkyl or acyl group of 1 to 7 carbon atoms,
    (ix) a group of the formula —NR$^{21}$R$^{22}$, wherein R$^{21}$ and R$^{22}$ are each, independently,
      (a) a hydrogen atom,
      (b) alkyl or acyl of 1 to 7 carbon atoms or cycloalkyl of 3 to 7 carbon atoms,
      (c) a group of the formula —(CH$_2$)$_m$COOH, wherein m is 0, 1 or 2, or (d) a group of the formula —(CH$_2$)$_n$COOR$^{23}$, wherein n is 0, 1 or 2, wherein R$^{23}$ is straight or branched alkyl of 1 to 6 carbon atoms, or wherein R$^{21}$ and R$^{22}$ constitute a saturated hydrocarbon bridge of 3 to 5 carbon atoms which together with the nitrogen atom between them form a heterocyclic ring, or (x) a quaternary group of the formula

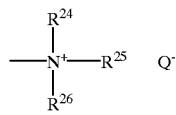

wherein R$^{24}$, R$^{25}$ and R$^{26}$ are each, independently, a branched or unbranched alkyl group of 1 to 7 carbon atoms and Q$^-$ is a chlorine, bromine or iodine counterion, (C) a branched or unbranched carboxylic acid group of 3 to 6 carbon atoms,
(D) a branched or unbranched phosphonic acid group of 2 to 6 carbon atoms,
(E) a branched or unbranched sulfonic acid group of 2 to 6 carbon atoms,
(F) an amidino group of the formula

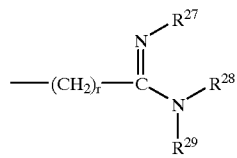

wherein r is 2, 3, 4, 5 or 6, and
R$^{27}$, R$^{28}$ and R$^{29}$ are each, independently, a hydrogen atom or alkyl of 1 to 3 carbon atoms, and wherein two of R$^{27}$, R$^{28}$ and R$^{29}$ may additionally constitute a saturated hydrocarbon bridge of 3 to 5 carbon atoms which together with the nitrogen atom(s) between them form a heterocyclic ring, (G) an guanidino group of the formula

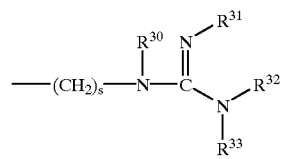

wherein s is 2, 3, 4, 5 or 6, and
R$^{30}$, R$^{31}$, R$^{32}$ and R$^{33}$ are each, independently, a hydrogen atom or alkyl of 1 to 3 carbon atoms, and wherein two of R$^{30}$, R$^{31}$, R$^{32}$ and R$^{33}$ may additionally constitute a saturated hydrocarbon bridge of 3 to 5 carbon atoms which together with the nitrogen atom(s) between them form a heterocyclic ring, (H) piperidyl, wherein the nitrogen atom of said group is optionally substituted with:
(i) alkyl of 1 to 3 carbon atoms,
(ii) a carboxylic ester group of 2 to 7 carbon atoms,
(iii) a carboxylic acid group of 2 to 5 carbon atoms,
(iv) a phosphonic acid group of 1 to 6 carbon atoms, or
(v) a sulfonic acid groups of 1 to 6 carbon atoms, or (I) aryl which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more hydrogen atoms of said aryl group may be optionally and independently replaced with:
(i) alkyl of 1 to 3 carbon atoms,
(ii) —COOH,
(iii) —SO$_2$OH,
(iv) —PO(OH)$_2$,
(v) a group of the formula —COOR$^7$, wherein R$^7$ is straight or branched alkyl of 1 to 5 carbon atoms or cycloalkyl of 3 to 5 carbon atoms,
(vi) a group of the formula —NR$^8$R$^9$, wherein R$^8$ and R$^9$ are each, independently, a hydrogen atom, alkyl of 1 to 6 carbon atoms, cycloalkyl of 3 to 6 carbon atoms or acyl of 1 to 7 carbon atoms, or wherein R$^8$ and R$^9$ constitute a saturated hydrocarbon bridge of 3 to 5 carbon atoms which together with the nitrogen atom between them form a heterocyclic ring,
(vii) a group of the formula —CONR$^{10}$R$^{11}$, wherein R$^{10}$ and R$^{11}$ are each, independently, a hydrogen atom, alkyl of 1 to 6 carbon atoms or cycloalkyl of 3 to 6 carbon atoms, or wherein R$^{10}$ and R$^{11}$ constitute a saturated hydrocarbon bridge of 3 to 5 carbon atoms which together with the nitrogen atom between them form a heterocyclic ring,
(viii) a group of the formula —OR$^{12a}$, wherein R$^{12a}$ is a hydrogen atom, or an alkyl or acyl group of 1 to 7 carbon atoms,
(ix) a group of the formula —SR$^{12b}$, wherein R$^{12b}$ is a hydrogen atom, or an alkyl or acyl group of 1 to 7 carbon atoms,
(x) cyano, or
(xi) an amidino group of the formula

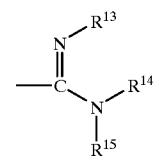

wherein R$^{13}$, R$^{14}$ and R$^{15}$ are each, independently, a hydrogen atom or alkyl of 1 to 3 carbon atoms, and wherein two of R$^{13}$, R$^{14}$ and R$^{15}$ may additionally constitute a saturated hydrocarbon bridge of 3 to 5 carbon atoms which together with the nitrogen atom(s) between them form a heterocyclic ring;

R$^2$ is:
(A) a hydrogen atom, or
(B) branched or unbranched alkyl of 1 to 3 carbon atoms or cycloalkyl of 3 to 5 carbon atoms wherein said alkyl or cycloalkyl group may optionally be substituted with:
(i) a group of the formula —OR$^{34}$, wherein R$^{34}$ is a hydrogen atom, or an alkyl or acyl group of 1 to 7 carbon atoms, or
(ii) a group of the formula —NR$^{35}$R$^{36}$, wherein R$^{35}$ and R$^{36}$ are each, independently, a hydrogen atom, alkyl of 1 to 2 carbon atoms, or acyl of 1 to 2 carbon atoms;

$R^3$ is a group of the formula —$(CR^{37}R^{38})_x(CR^{39}R^{40})_yR^{41}$, wherein;

x and y are each independently 0 or 1, $R^{37}$, $R^{38}$ and $R^{39}$ are each, independently:
(A) a hydrogen atom,
(B) a group of the formula —$OR^{42}$, wherein $R^{42}$ is a hydrogen atom, or an alkyl or acyl group of 1 to 7 carbon atoms, or
(C) branched or unbranched alkyl of 1 to 3 carbon atoms or cycloalkyl of 3 to 5 carbon atoms, $R^{40}$ is:
(A) a hydrogen atom,
(B) a group of the formula —$OR^{42}$, wherein $R^{42}$ is a hydrogen atom, or an alkyl or acyl group of 1 to 7 carbon atoms,
(C) branched or unbranched alkyl of 1 to 3 carbon atoms or cycloalkyl of 3 to 5 carbon atoms, or
(D) aryl which is selected from the class consisting of phenyl, 2 naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl, wherein one or more of the hydrogen atoms of said aryl group may be optionally and independently replaced with:
(i) $R^{43}$, which is aryl selected from the class consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl, wherein one or more of the hydrogen atoms of said aryl group may be optionally and independently replaced with:
  (a) branched or unbranched alkyl of 1 to 6 carbon atoms or cycloalkyl of 3 to 6 carbon atoms, which alkyl or cycloakyl group may be mono- or polysubstituted with halogen or oxo,
  (b) —COOH,
  (c) —$SO_2H$,
  (d) —$PO(OH)_2$,
  (e) a group of the formula —$COOR^{44}$, wherein $R^{44}$ is straight or branched alkyl of 1 to 5 carbon atoms or cycloalkyl of 3 to 5 carbon atoms,
  (f) a group of the formula —$NR^{45}R^{46}$, wherein $R^{45}$ and $R^{46}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein $R^{45}$ and $R^{46}$ constitute a saturated hydrocarbon bridge of 3 to 5 carbon atoms which together with the nitrogen atom between them form a heterocyclic ring,
  (g) a group of the formula —$CONR^{47}R^{48}$, wherein $R^{47}$ and $R^{48}$ are each independently a hydrogen atom, alkyl or fluoroalkyl of 1 to 6 carbon atoms or cycloalkyl of 3 to 6 carbon atoms, or wherein $R^{47}$ and $R^{48}$ constitute a saturated hydrocarbon bridge of 3 to 5 carbon atoms which together with the nitrogen atom between them form a heterocyclic ring,
  (h) a group of the formula —$OR^{49}$, wherein $R^{49}$ is a hydrogen atom, or an alkyl, fluoroalkyl or acyl group of 1 to 7 carbon atoms,
  (i) a group of the formula —$SR^{50}$, wherein $R^{50}$ is a hydrogen atom, or an alkyl, fluoroalkyl or acyl group of 1 to 7 carbon atoms,
  (j) cyano,
  (k) nitro,
  (l) an amidino group of the formula

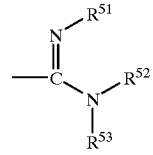

wherein $R^{51}$, $R^{52}$ and $R^{53}$ are each, independently, a hydrogen atom or alkyl of 1 to 3 carbon atoms, and wherein two of $R^{51}$, $R^{52}$ and $R^{53}$ may additionally constitute a saturated hydrocarbon bridge of 3 to 5 carbon atoms which together with the nitrogen atom(s) between them form a heterocyclic ring, or
  (m) halogen,
(ii) methyl, which may be mono- or polysubstituted with fluorine atoms and additionally may be monosubstituted with $R^{43}$,
(iii) branched or unbranched alkyl of 2 to 6 carbon atoms or cycloalkyl of 3 to 6 carbon atoms, which alkyl or cycloakyl group may be mono- or polysubstituted with halogen or oxo,
(iv) a group of the formula —$COOR^{54}$, wherein $R^{54}$ is straight or branched alkyl of 1 to 5 carbon atoms or cycloalkyl of 3 to 5 carbon atoms,
(v) a group of the formula —$NR^{55}R^{56}$, wherein $R^{55}$ and $R^{56}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein $R^{55}$ and $R^{56}$ constitute a saturated hydrocarbon bridge of 3 to 5 carbon atoms which together with the nitrogen atom between them form a heterocyclic ring, and wherein one of $R^{55}$ and $R^{56}$ may additionally be the group $R^{43}$,
(vi) a group of the formula —$CONR^{57}R^{58}$, wherein $R^{57}$ and $R^{58}$ are each, independently, a hydrogen atom, alkyl or fluoroalkyl of 1 to 6 carbon atoms or cycloalkyl of 3 to 6 carbon atoms, or wherein $R^{57}$ and $R^{58}$ constitute a saturated hydrocarbon bridge of 3 to 5 carbon atoms which together with the nitrogen atom between them form a heterocyclic ring, and wherein one of $R^{57}$ and $R^{58}$ may additionally be the group $R^{43}$, (vii) a group of the formula —$COR^{59}$, wherein $R^{59}$ is a hydrogen atom, straight or branched alkyl of 1 to 5 carbon atoms, cycloalkyl of 3 to 5 carbon atoms or $R^{43}$, (viii) a group of the formula —$OR^{60}$, wherein $R^{60}$ is a hydrogen atom, an alkyl, fluoroalkyl or acyl group of 1 to 7 carbon atoms, or $R^{43}$, (ix) a group of the formula —$SR^{61}$, wherein $R^{61}$ is a hydrogen atom, an alkyl, fluoroalkyl or acyl group of 1 to 7 carbon atoms, or $R^{43}$, (x) cyano, (xi) nitro, or (xii) halogen, $R^{41}$ is:

aryl selected from the class consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl, wherein one or more of the hydrogen atoms of said aryl group may be optionally and independently replaced with:

(A) $R^{62}$, which is aryl selected from the class consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl, wherein one or more of the hydrogen atoms of said aryl group may be optionally and independently replaced with:

(i) branched or unbranched alkyl of 1 to 6 carbon atoms or cycloalkyl of 3 to 6 carbon atoms, which alkyl or cycloakyl group may be mono- or polysubstituted with halogen or oxo, (ii) —COOH, (iii) —$SO_2H$, (iv) —$PO(OH)_2$, (v) a group of the formula —$COOR^{63}$, wherein $R^{63}$ is straight or branched alkyl of 1 to 5 carbon atoms or cycloalkyl of 3 to 5 carbon atoms, (vi) a group of the formula —$NR^{64}R^{65}$, wherein $R^{64}$ and $R^{65}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein $R^{64}$ and $R^{65}$ constitute a saturated hydrocarbon bridge of 3 to 5 carbon atoms which together with the nitrogen atom between them form a heterocyclic ring, (vii) a group of the formula —$CONR^{66}R^{67}$, wherein $R^{66}$ and $R^{67}$ are each, independently, a hydrogen atom, alkyl or fluoroalkyl of 1 to 6 carbon atoms or cycloalkyl of 3 to 6 carbon atoms, or wherein $R^{66}$ and $R^{67}$ constitute a saturated hydrocarbon bridge of 3 to 5 carbon atoms which together with the nitrogen atom between them form a heterocyclic ring, (viii) a group of the formula —$OR^{68}$, wherein $R^{68}$ is a hydrogen atom, or an alkyl, fluoroalkyl or acyl group of 1 to 7 carbon atoms, (ix) a group of the formula —$SR^{69}$, wherein $R^{69}$ is a hydrogen atom, or an alkyl, fluoroalkyl or acyl group of 1 to 7 carbon atoms, (x) cyano, (xi) nitro, or (xii) an amidino group of the formula

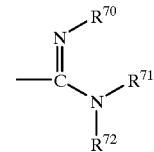

wherein $R^{70}$, $R^{71}$ and $R^{72}$ are each, independently, a hydrogen atom or alkyl or fluoroalkyl of 1 to 3 carbon atoms, and wherein two of $R^{70}$, $R^{71}$ and $R^{72}$ may additionally constitute a saturated hydrocarbon bridge of 3 to 5 carbon atoms which together with the nitrogen atom(s) between them form a heterocyclic ring, or (xiii) halogen, (B) methyl, which may be mono- or polysubstituted with fluorine atoms and additionally may be monosubstituted with $R^{62}$, (C) branched or unbranched alkyl of 2 to 6 carbon atoms or cycloalkyl of 3 to 6 carbon atoms, which alkyl or cycloakyl group may be mono- or polysubstituted with halogen or oxo, (D) a group of the formula —$COOR^{73}$, wherein $R^{73}$ is straight or branched alkyl of 1 to 5 carbon atoms or cycloalkyl of 3 to 5 carbon atoms, (E) a group of the formula —$NR^{74}R^{75}$, wherein $R^{74}$ and $R^{75}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein $R^{74}$ and $R^{75}$ constitute a saturated hydrocarbon bridge of 3 to 5 carbon atoms which together with the nitrogen atom between them form a heterocyclic ring, and wherein one of $R^{74}$ and $R^{75}$ may additionally be the group $R^{62}$, (F) a group of the formula —$CONR^{76}R^{77}$, wherein $R^{76}$ and $R^{77}$ are each, independently, a hydrogen atom, alkyl or fluoroalkyl of 1 to 6 carbon atoms or cycloalkyl of 3 to 6 carbon atoms, or wherein $R^{76}$ and $R^{77}$ constitute a saturated hydrocarbon bridge of 3 to 5 carbon atoms which together with the nitrogen atom between them form a heterocyclic ring, and wherein one of $R^{76}$ and $R^{77}$ may additionally be the group $R^{62}$, (G) a group of the formula —$COR^{78}$, wherein $R^{78}$ is a hydrogen atom, straight or branched alkyl of 1 to 5 carbon atoms, cycloalkyl of 3 to 5 carbon atoms or $R^{62}$, (H) a group of the formula —$OR^{79}$, wherein $R^{79}$ is a hydrogen atom, an alkyl, fluoroalkyl or acyl group of 1 to 7 carbon atoms, or $R^{62}$, (I) a group of the formula —$SR^{80}$, wherein $R^{80}$ is a hydrogen atom, an alkyl, fluoroalkyl or acyl group of 1 to 7 carbon atoms, or $R^{62}$, (J) cyano, (K) nitro, or (L) halogen;

$R^4$ is Cl or trifluoromethyl; and, $R^6$ is a fluorine, chlorine, bromine or iodine atom, methyl or trifluoromethyl, CN or $NO_2$;

or a pharmaceutically acceptable salt thereof.

Preferred are compounds of the formula I wherein:

Y is an oxygen or sulfur atom;

Z is an oxygen or sulfur atom;

X is a divalent group of the formula >$CHR^1$, >$NR^1$, >$CHSO_2R^1$, or >$NSO_2R^1$, or an oxygen or sulfur atom, wherein $R^1$ is:

(A) a hydrogen atom, (B) branched or unbranched alkyl of 1 to 6 carbon atoms or cycloalkyl of 3 to 6 carbon atoms, which alkyl or cycloakyl group may be monosubstituted with:
 (i) halogen,
 (ii) oxo,
 (iii) aryl selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more hydrogen atoms of said aryl group may be optionally and independently replaced with:
  (a) alkyl of 1 to 3 carbon atoms,
  (b) —COOH,
  (c) —$SO_2H$,
  (d) —$PO(OH)_2$,
  (e) a group of the formula —$COOR^7$, wherein $R^7$ is straight or branched alkyl of 1 to 5 carbon atoms or cycloalkyl of 3 to 5 carbon atoms,
  (f) a group of the formula —$NR^8R^9$, wherein $R^8$ and $R^9$ are each, independently, a hydrogen atom, alkyl of 1 to 6 carbon atoms, cycloalkyl of 3 to 6 carbon atoms or acyl of 1 to 7 carbon atoms, or wherein $R^8$ and $R^9$ constitute a saturated hydrocarbon bridge of 3 to 5 carbon atoms which together with the nitrogen atom between them form a heterocyclic ring,
  (g) a group of the formula —$CONR^{10}R^{11}$, wherein $R^{10}$ and $R^{11}$ are each, independently, a hydrogen atom, alkyl of 1 to 6 carbon atoms or cycloalkyl of 3 to 6 carbon atoms, or wherein $R^{10}$ and $R^{11}$ constitute a saturated hydrocarbon bridge of 3 to 5 carbon atoms which together with the nitrogen atom between them form a heterocyclic ring,
  (h) a group of the formula —$OR^{12a}$, wherein $R^{12a}$ is a hydrogen atom, or an alkyl or acyl group of 1 to 7 carbon atoms,
  (i) a group of the formula —$SR^{12b}$, wherein $R^{12b}$ is a hydrogen atom, or an alkyl or acyl group of 1 to 7 carbon atoms,
  (j) cyano, or
  (k) an amidino group of the formula

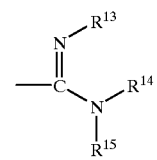

wherein $R^{13}$, $R^{14}$ and $R^{15}$ are each, independently, a hydrogen atom or alkyl of 1 to 3 carbon atoms and wherein two of $R^{13}$, $R^{14}$ and $R^{15}$ may additionally constitute a saturated hydrocarbon bridge of 3 to 5 carbon atoms which together with the nitrogen atom(s) between them form a heterocyclic ring, (iv) a group of the formula —$COOR^{16}$, wherein $R^{16}$ is straight or branched alkyl of 1 to 7 carbon atoms or cycloalkyl of 3 to 6 carbon atoms, (v) cyano, (vi) a group of the formula —$CONR^{17}R^{18}$, wherein $R^{17}$ and $R^{18}$ are each, independently, a hydrogen atom, alkyl of 1 to 6 carbon atoms or cycloalkyl of 3 to 6 carbon atoms, or wherein $R^{17}$ and $R^{18}$ constitute a saturated hydrocarbon bridge of 3 to 5 carbon atoms which together with the nitrogen atom between them form a heterocyclic ring, (vii) a group of the formula —$OR^{19}$, wherein $R^{19}$ is a hydrogen atom, or an alkyl or acyl group of 1 to 7 carbon atoms, (viii) a group of the formula —$SR^{20}$, wherein $R^{20}$ is a hydrogen atom, or an alkyl or acyl group of 1 to 7 carbon atoms, (ix) a group of the formula —$NR^{21}R^{22}$, wherein $R^{21}$ and $R^{22}$ are each, independently:
 (a) a hydrogen atom,
 (b) alkyl or acyl of 1 to 7 carbon atoms or cycloalkyl of 3 to 7 carbon atoms,
 (c) a group of the formula —$(CH_2)_mCOOH$, wherein m is 0, 1 or 2, or
 (d) a group of the formula —$(CH_2)_nCOOR^{23}$, wherein n is 0, 1 or 2, wherein $R^{23}$ is straight or branched alkyl of 1 to 6 carbon atoms, or wherein $R^{21}$ and $R^{22}$ constitute a saturated hydrocarbon bridge of 3 to 5 carbon atoms which together with the nitrogen atom between them form a heterocyclic ring, or (x) a quaternary group of the formula

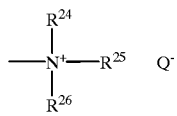

wherein $R^{24}$, $R^{25}$ and $R^{26}$ are each, independently, a branched or unbranched alkyl group of 1 to 7 carbon atoms and $Q_-$ is a chlorine, bromine or iodine counterion,
(C) a branched or unbranched carboxylic acid group of 3 to 6 carbon atoms,
(D) a branched or unbranched phosphonic acid group of 2 to 6 carbon atoms,
(E) a branched or unbranched sulfonic acid group of 2 to 6 carbon atoms,
(F) an amidino group of the formula

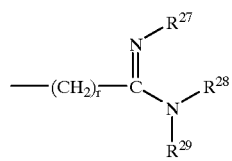

wherein r is 2, 3, 4, 5 or 6, and
$R^{27}$, $R^{28}$ and $R^{29}$ are each, independently, a hydrogen atom or alkyl of 1 to 3 carbon atoms and wherein two of $R^{27}$, $R^{28}$ and $R^{29}$ may additionally constitute a saturated hydrocarbon bridge of 3 to 5 carbon atoms which together with the nitrogen atom(s) between them form a heterocyclic ring,
(G) an guanidino group of the formula

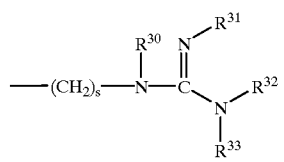

wherein s is 2, 3, 4, 5 or 6, and
$R^{30}$, $R^{31}$, $R^{32}$ and $R^{33}$ are each independently a hydrogen atom or alkyl of 1 to 3 carbon atoms and wherein two of $R^{30}$, $R^{31}$, $R^{32}$ and $R^{33}$ may additionally constitute a saturated hydrocarbon bridge of 3 to 5 carbon atoms which together with the nitrogen atom(s) between them form a heterocyclic ring, or
(H) piperidyl, wherein the nitrogen atom of said group is optionally substituted with:
(i) alkyl of 1 to 3 carbon atoms,
(ii) a carboxylic ester group of 2 to 7 carbon atoms,
(iii) a carboxylic acid group of 2 to 5 carbon atoms,
(iv) a phosphonic acid group of 1 to 6 carbon atoms, or
(v) a sulfonic acid group of 1 to 6 carbon atoms;
$R^2$ is:
(A) a hydrogen atom, or
(B) methyl;
$R^3$ is a group of the formula —$CH_2R^{41}$, wherein:
$R^{41}$ is:
aryl selected from the class consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl, wherein one or more of the hydrogen atoms of said aryl group are necessarily and independently replaced with:
(A) $R^{62}$, which is aryl selected from the class consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl, wherein one or more of the hydrogen atoms of said aryl group may be optionally and independently replaced with:
(i) branched or unbranched alkyl of 1 to 6 carbon atoms or cycloalkyl of 3 to 6 carbon atoms, which alkyl or cycloakyl group may be mono- or polysubstituted with halogen or oxo,
(ii) —COOH,
(iii) —$SO_2OH$,
(iv) —$PO(OH)_2$,
(v) a group of the formula —$COOR^{63}$, wherein $R^{63}$ is straight or branched alkyl of 1 to 5 carbon atoms or cycloalkyl of 3 to 5 carbon atoms,
(vi) a group of the formula —$NR^{64}R^{65}$, wherein R64 and $R^{65}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein $R^{64}$ and $R^{65}$ constitute a saturated hydrocarbon bridge of 3 to 5 carbon atoms which together with the nitrogen atom between them form a heterocyclic ring,
(vii) a group of the formula —$CONR^{66}R^{67}$, wherein $R^{66}$ and $R^{67}$ are each, independently, a hydrogen atom, alkyl or fluoroalkyl of 1 to 6 carbon atoms or cycloalkyl of 3 to 6 carbon atoms, or wherein $R^{66}$ and $R^{67}$ constitute a saturated hydrocarbon bridge of 3 to 5 carbon atoms which together with the nitrogen atom between them form a heterocyclic ring,
(viii) a group of the formula —$OR^{68}$, wherein $R^{68}$ is a hydrogen atom, or an alkyl, fluoroalkyl or acyl group of 1 to 7 carbon atoms,
(ix) a group of the formula —$SR^{69}$, wherein $R^{69}$ is a hydrogen atom, or an alkyl, fluoroalkyl or acyl group of 1 to 7 carbon atoms, (x) cyano,
(xi) nitro,
(xii) an amidino group of the formula

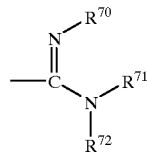

where in $R^{70}$, $R^{71}$ and $R^{72}$ are each, independently, a hydrogen atom or alkyl or fluoroalkyl of 1 to 3 carbon atoms, and wherein two of $R^{70}$, $R^{71}$ and $R^{72}$ may additionally constitute a saturated hydrocarbon bridge of 3 to 5 carbon atoms which together with the nitrogen atom(s) between them form a heterocyclic ring, or
(xiii) halogen,
(B) methyl, which may be mono- or polysubstituted with fluorine atoms and additionally may be monosubstituted with $R^{62}$,
(C) branched or unbranched alkyl of 2 to 6 carbon atoms or cycloalkyl of 3 to 6 carbon atoms, which alkyl or cycloakyl group may be mono- or polysubstituted with halogen or oxo,
(D) a group of the formula —$COOR^{73}$, wherein $R^{73}$ is straight or branched alkyl of 1 to 5 carbon atoms or cycloalkyl of 3 to 5 carbon atoms,
(E) a group of the formula —$NR^{74}R^{75}$, wherein $R^{74}$ and $R^{75}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein $R^{74}$ and $R^{75}$ constitute a saturated hydrocarbon bridge of 3 to 5 carbon atoms which together with the nitrogen atom between them form a heterocyclic ring, and wherein one of $R^{74}$ and $R^{75}$ may additionally be the group $R^{62}$,
(F) a group of the formula —$CONR^{76}R^{77}$, wherein $R^{76}$ and $R^{77}$ are each, independently, a hydrogen atom, alkyl or fluoroalkyl of 1 to 6 carbon atoms or cycloalkyl of 3 to 6 carbon atoms, or wherein $R^{76}$ and $R^{77}$ constitute a saturated hydrocarbon bridge of 3 to 5 carbon atoms which together with the nitrogen atom between them form a heterocyclic ring, and wherein one of $R^{76}$ and $R^{77}$ may additionally be the group $R^{62}$,
(G) a group of the formula —$COR^{78}$, wherein $R^{78}$ is a hydrogen atom, straight or branched alkyl of 1 to 5 carbon atoms, cycloalkyl of 3 to 5 carbon atoms or $R^{62}$,
(H) a group of the formula —$OR^{79}$, wherein $R^{79}$ is a hydrogen atom, an alkyl, fluoroalkyl or acyl group of 1 to 7 carbon atoms, or $R^{62}$,
(I) a group of the formula —$SR^{80}$, wherein $R^{80}$ is a hydrogen atom, an alkyl, fluoroalkyl or acyl group of 1 to 7 carbon atoms, or $R^{62}$,
(J) cyano,
(K) nitro, or
(L) halogen;
$R^4$ is Cl or trifluoromethyl; and,
$R^6$ is a fluorine, chlorine, bromine or iodine atom, methyl or trifluoromethyl, CN or $NO_2$;
or a pharmaceutically acceptable salt thereof.
More preferred are compounds of the formula I wherein:

Y is an oxygen atom;
Z is an oxygen atom;
X is a divalent group of the formula >$CHR^1$ or >$NR^1$,
wherein $R^1$ is:
(A) a hydrogen atom,
(B) branched or unbranched alkyl of 1 to 6 carbon atoms or cycloalkyl of 3 to 6 carbon atoms, which alkyl or cycloakyl group may be monosubstituted with:
(i) oxo,
(ii) aryl selected from the class consisting of phenyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl and triazinyl, wherein one or more hydrogen atoms of said aryl group may be optionally and independently replaced with:
(a) alkyl of 1 to 3 carbon atoms,
(b) —COOH,
(c) —$SO_2OH$,
(d) —$PO(OH)_2$,
(e) a group of the formula —$COOR^7$, wherein $R^7$ is straight or branched alkyl of 1 to 5 carbon atoms or cycloalkyl of 3 to 5 carbon atoms,
(f) a group of the formula —$NH_2$,
(g) a group of the formula —$CONH_2$,
(h) a group of the formula —$OR^{12a}$, wherein $R^{12a}$ is a hydrogen atom or a methyl,
(i) an amidino group of the formula

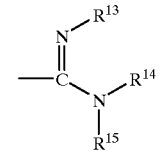

wherein $R^{13}$, $R^{14}$ and $R^{15}$ are each hydrogen atoms,
(j) a group of the formula —$COOR^{16}$, wherein $R^{16}$ is straight or branched alkyl of 1 to 7 carbon atoms or cycloalkyl of 3 to 6 carbon atoms,
(k) a group of the formula —$OR^{19}$, wherein $R^{19}$ is a hydrogen atom, or an alkyl or acyl group of 1 to 7 carbon atoms, or
(l) a quaternary group of the formula

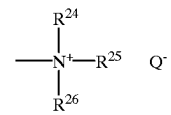

wherein $R^{24}$, $R^{25}$ and $R^{26}$ are each methyl and $Q^-$ is a chlorine, bromine or iodine counterion,
(C) a branched or unbranched carboxylic acid group of 3 to 6 carbon atoms,
(D) a branched or unbranched phosphonic acid group of 2 to 6 carbon atoms,
(E) a branched or unbranched sulfonic acid group of 2 to 6 carbon atoms, (F) an amidino group of the formula

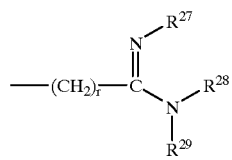

wherein r is 2, 3, 4, 5 or 6, and
$R^{27}$, $R^{28}$ and $R^{29}$ are each hydrogen atoms,
(G) an guanidino group of the formula

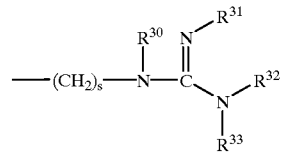

wherein s is 2, 3, 4, 5 or 6,
$R^{30}$, $R^{31}$, $R^{32}$ and $R^{33}$ are each hydrogen atoms, or
(H) piperidyl, wherein the nitrogen atom of said group is optionally substituted with:
(i) alkyl of 1 to 3 carbon atoms,
(ii) a carboxylic ester group of 2 to 7 carbon atoms,
(iii) a carboxylic acid group of 2 to 5 carbon atoms,
(iv) a phosphonic acid group of 1 to 6 carbon atoms, or
(v) a sulfonic acid group of 1 to 6 carbon atoms;
$R^2$ is:
(A) a hydrogen atom, or
(B) methyl;
$R^3$ is a group of the formula —$CH_2R^{41}$, wherein $R^{41}$ is
aryl selected from the class consisting of phenyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl and triazinyl, wherein one or more of the hydrogen atoms of said aryl group are necessarily and independently replaced with:
(A) $R^{62}$, which is aryl selected from the class consisting of phenyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl and triazinyl, wherein one or more of the hydrogen atoms of said aryl group may be optionally and independently replaced with:
(i) methyl,
(ii) —COOH,
(iii) —$SO_2OH$,
(iv) —$PO(OH)_2$,
(v) a group of the formula —$COOR^{63}$, wherein $R^{63}$ is methyl,
(vi) a group of the formula —$NR^{64}R^{65}$, wherein $R^{64}$ and $R^{65}$ are each, independently, a hydrogen atom or methyl,
(vii) a group of the formula —$CONR^{66}R^{67}$, wherein $R^{66}$ and $R^{67}$ are each, independently, a hydrogen atom or methyl,
(viii) a group of the formula —$CR^{68}$, wherein $R^{68}$ is a hydrogen atom or methyl,
(ix) a group of the formula —$SR^{69}$, wherein $R^{69}$ is a hydrogen atom or methyl,
(x) cyano,
(xi) nitro, or
(xii) halogen,
(B) methyl, which may be mono- or polysubstituted with fluorine atoms and which additionally may be monosubstituted with $R^{62}$,
(C) branched or unbranched alkyl of 2 to 6 carbon atoms or cycloalkyl of 3 to 6 carbon atoms, which alkyl or cycloakyl group may be mono- or polysubstituted with halogen or oxo,
(D) a group of the formula —$COOR^{73}$, wherein $R^{73}$ is methyl,
(E) a group of the formula —$NR^{74}R^{75}$, wherein $R^{74}$ and $R^{75}$ are each, independently, a hydrogen atom or methyl, and wherein one of $R^{74}$ and $R^{75}$ may additionally be the group $R^{62}$,
(F) a group of the formula —$CONR^{76}R^{77}$, wherein $R^{76}$ and $R^{77}$ are each, independently, a hydrogen atom or methyl, and wherein one of $R^{76}$ and $R^{77}$ may additionally be the group $R^{62}$,
(G) a group of the formula —$COR^{78}$, wherein $R^{78}$ is a hydrogen atom, methyl or $R^{62}$,
(H) a group of the formula —$CR^{79}$, wherein $R^{79}$ is a hydrogen atom, methyl or $R^{62}$,
(I) a group of the formula —$SR^{80}$, wherein $R^{80}$ is a hydrogen atom, methyl or $R^{62}$,
(J) cyano,
(K) nitro, or
(L) halogen;
$R^4$ is Cl or trifluoromethyl; and,
$R^6$ is a fluorine, chlorine, bromine or iodine atom, methyl or trifluoromethyl, CN or $NO_2$;
or a pharmaceutically acceptable salt thereof.
Even more preferred are compounds of the formula I:
wherein:
Y is an oxygen atom;
Z is an oxygen atom;
X is a divalent group of the formula >$CHR^1$ or >$NR^1$,
wherein $R^1$ is:
(A) a hydrogen atom,
(B) branched or unbranched alkyl of 1 to 6 carbon atoms or cycloalkyl of 3 to 6 carbon atoms, which alkyl or cycloakyl group may be monosubstituted with:
(i) oxo,
(ii) aryl selected from the class consisting of phenyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl and triazinyl, wherein one or more hydrogen atoms of said aryl group may be optionally and independently replaced with:
(a) alkyl of 1 to 3 carbon atoms,
(b) —COOH,
(c) —$SO_2OH$,
(d) —$PO(OH)_2$,
(e) a group of the formula —$COOR^7$, wherein $R^7$ is straight or branched alkyl of 1 to 5 carbon atoms or cycloalkyl of 3 to 5 carbon atoms,
(f) a group of the formula —$NH_2$,
(g) a group of the formula —$CONH_2$,
(h) a group of the formula —$OR^{12a}$, wherein $R^{12a}$ is a hydrogen atom or a methyl, (i) an amidino group of the formula

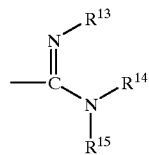

wherein $R^{13}$, $R^{14}$ and $R^{15}$ are each hydrogen atoms,
(j) a group of the formula —COOR$^{16}$, wherein $R^{16}$ is straight or branched alkyl of 1 to 7 carbon atoms or cycloalkyl of 3 to 6 carbon atoms,
(k) a group of the formula —OR$^9$, wherein $R^{19}$ is a hydrogen atom, or an alkyl or acyl group of 1 to 7 carbon atoms, or
(l) a quaternary group of the formula

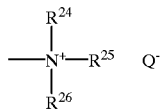

wherein $R^{24}$, $R^{25}$ and $R^{26}$ are each methyl and $Q^-$ is a chlorine, bromine or iodine counterion,
(C) a branched or unbranched carboxylic acid group of 3 to 6 carbon atoms,
(D) a branched or unbranched phosphonic acid group of 2 to 6 carbon atoms,
(E) a branched or unbranched sulfonic acid group of 2 to 6 carbon atoms,
(F) an amidino group of the formula

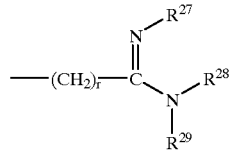

wherein r is 2, 3, 4, 5 or 6, and
$R^{27}$, $R^{28}$ and $R^{29}$ are each hydrogen atoms,
(G) an guanidino group of the formula

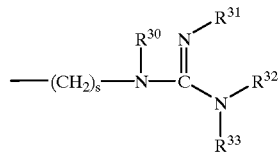

wherein s is 2, 3, 4, 5 or 6,
$R^{30}$, $R^{31}$, $R^{32}$ and $R^{33}$ are each hydrogen atoms, or
(H) piperidyl, wherein the nitrogen atom of said group is optionally substituted with:
(i) alkyl of 1 to 3 carbon atoms,
(ii) a carboxylic ester group of 2 to 7 carbon atoms,
(iii) a carboxylic acid group of 2 to 5 carbon atoms,
(iv) a phosphonic acid group of 1 to 6 carbon atoms, or
(v) a sulfonic acid group of 1 to 6 carbon atoms;
$R^2$ is:

(A) a hydrogen atom, or
(B) methyl;
$R^3$ is a group of the formula —CH$_2$R$^{41}$, wherein $R^{41}$ is
aryl selected from the class consisting of phenyl, thiophenyl, pyridyl, pyrimidinyl, furyl, oxazolyl, thiazolyl, isoxazolyl, isothiazolyl, oxadiazolyl, thiadiazolyl, pyridazinyl, and pyrazinyl, wherein one or more of the hydrogen atoms of said aryl group are necessarily and independently replaced with:
(A) $R^{62}$, which is aryl selected from the class consisting of phenyl, thiophenyl, pyridyl, pyrimidinyl, furyl, oxazolyl, thiazolyl, isoxazolyl, isothiazolyl, oxadiazolyl, thiadiazolyl, pyridazinyl, and pyrazinyl, wherein one or more of the hydrogen atoms of said aryl group may be optionally and independently replaced with:
(i) methyl,
(ii) —COOH,
(iii) a group of the formula —COOR$^{63}$, wherein $R^{63}$ is methyl,
(iv) a group of the formula —CR$^{68}$, wherein $R^{68}$ is a hydrogen atom or methyl, or
(v) halogen,
(B) methyl, which may be mono- or polysubstituted with fluorine atoms or which may be monosubstituted with $R^{62}$,
(C) branched or unbranched alkyl of 2 to 6 carbon atoms or cycloalkyl of 3 to 6 carbon atoms, which alkyl or cycloakyl group may be mono- or polysubstituted with halogen or oxo,
(D) a group of the formula —COOR$^{73}$, wherein $R^{73}$ is methyl,
(E) a group of the formula —CONR$^{76}$R$^{77}$, wherein $R^{76}$ and $R^{77}$ are each methyl, and wherein one of $R^{76}$ and $R^{77}$ is methyl and the other is the group $R^{62}$,
(F) a group of the formula —COR$^{78}$, wherein $R^{78}$ is a hydrogen atom, methyl or $R^{62}$,
(G) a group of the formula —CR$^{79}$, wherein $R^{79}$ is a hydrogen atom, methyl or $R^{62}$,
(H) cyano,
(I) nitro, or
(J) halogen;
$R^4$ is Cl or trifluoromethyl; and,
$R^6$ is Cl or trifluoromethyl;
or a pharmaceutically acceptable salt thereof.
Still more preferred are compounds of the formula I wherein:
Y is an oxygen atom;
Z is an oxygen atom;
X is a divalent group of the formula >CHR$^1$ or >NR$^1$, wherein $R^1$ is:
(A) a hydrogen atom,
(B) branched or unbranched alkyl of 1 to 6 carbon atoms or cycloalkyl of 3 to 6 carbon atoms, which alkyl or cycloakyl group may be monosubstituted with:
(i) oxo,
(ii) aryl selected from the class consisting of phenyl or pyridyl, wherein one or more hydrogen atoms of said aryl group may be optionally and independently replaced with:
(a) alkyl of 1 to 3 carbon atoms,
(b) —COOH,
(c) —SO$_2$OH, (d) —PO(OH)$_2$,
(e) a group of the formula —OR$^{12a}$, wherein R$^{12a}$ is a hydrogen atom or a methyl,
(f) an amidino group of the formula

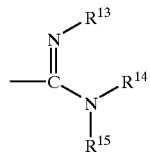

wherein R$^{13}$, R$^{14}$ and R$^{15}$ are each hydrogen atoms,
(iii) a group of the formula —OR$^{19}$, wherein R$^{19}$ is a hydrogen atom, or an alkyl or acyl group of 1 to 7 carbon atoms, or
(iv) a quaternary group of the formula

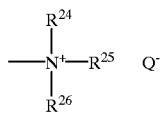

wherein R$^{24}$, R$^{25}$ and R$^{26}$ are each methyl and Q$^-$ is a chlorine, bromine or iodine counterion,
(C) a branched or unbranched carboxylic acid group of 3 to 6 carbon atoms,
(D) a branched or unbranched phosphonic acid group of 2 to 6 carbon atoms,
(E) a branched or unbranched sulfonic acid group of 2 to 6 carbon atoms,
(F) an amidino group of the formula

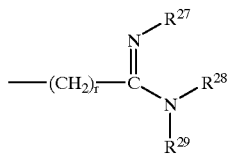

wherein r is 2, 3, 4, 5 or 6, and
R$^{27}$, R$^{28}$ and R$^{29}$ are each hydrogen atoms,
(G) an guanidino group of the formula

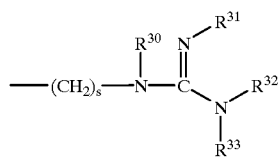

wherein s is 2, 3, 4, 5 or 6,
R$^{30}$, R$^{31}$, R$^{32}$ and R$^{33}$ are each hydrogen atoms, or
(H) piperidyl, wherein the nitrogen atom of said group is optionally substituted with:
(i) alkyl of 1 to 3 carbon atoms,
(ii) a carboxylic ester group of 2 to 7 carbon atoms,
(iii) a carboxylic acid group of 2 to 5 carbon atoms,
(iv) a phosphonic acid group of 1 to 6 carbon atoms, or
(v) a sulfonic acid group of 1 to 6 carbon atoms;
R$^2$ is:

(A) a hydrogen atom, or
(B) methyl;
R$^3$ is a group of the formula —CH$_2$R$^{41}$, wherein
R$^{41}$ is
aryl selected from the class consisting of phenyl or pyridyl, wherein one or more of the hydrogen atoms of said aryl group are necessarily and independently replaced with:
(A) R$^{62}$, which is aryl selected from the class consisting of phenyl, or pyridyl, wherein one or more of the hydrogen atoms of said aryl group may be optionally and independently replaced with:
(i) methyl,
(ii) —COOH
(iii) a group of the formula —COOR$^{63}$, wherein R$^{63}$ is methyl,
(iv) a group of the formula —OR$^{68}$, wherein R$^{68}$ is a hydrogen atom or methyl, or
(v) halogen,
(B) methyl, which may be mono- or polysubstituted with fluorine atoms or which may be monosubstituted with R$^{62}$,
(C) branched or unbranched alkyl of 2 to 6 carbon atoms or cycloalkyl of 3 to 6 carbon atoms, which alkyl or cycloakyl group may be mono- or polysubstituted with fluorine or oxo,
(D) a group of the formula —COOR$^{73}$, wherein R$^{73}$ is methyl,
(E) a group of the formula —CONR$^{76}$R$^{77}$, wherein R$^{76}$ and R$^{77}$ are each methyl, and wherein one of R$^{76}$ and R$^{77}$ is methyl and the other is the group R$^{62}$,
(F) a group of the formula —COR$^{78}$, wherein R$^{78}$ is a hydrogen atom, methyl or R$^{62}$,
(G) a group of the formula —OR$^{79}$, wherein R$^{79}$ is a hydrogen atom, methyl or R$^{62}$,
(H) cyano,
(I) nitro, or
(J) halogen;
R$^4$ is Cl or trifluoromethyl; and,
R$^6$ is Cl or trifluoromethyl;
or a pharmaceutically acceptable salt thereof.
Especially preferred are compounds of the formula I wherein:
Y is an oxygen atom;
Z is an oxygen atom;
X is a divalent group of the formula >CHR$^1$ or >NR$^1$,
R$^1$ is:
(A) a hydrogen atom,
(B) alkyl of 1 to 2 carbon atoms which may be monosubstituted with:
(i) oxo,
(ii) aryl selected from the class consisting of phenyl or pyridyl, wherein one hydrogen atom of said aryl group may be optionally replaced with:
(a) alkyl of 1 to 3 carbon atoms,
(b) —COOH,
(c) —SO$_2$OH,
(d) —PO(OH)$_2$,
(e) a group of the formula —OR$^{12a}$, wherein R$^{12a}$ is a hydrogen atom or a methyl, or (f) an amidino group of the formula

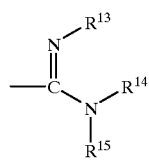

wherein $R^{13}$, $R^{14}$ and $R^{15}$ are each hydrogen atoms, or
(iii) a group of the formula —$OR^{19}$, wherein $R^{19}$ is a hydrogen atom or methyl,
(C) a branched or unbranched carboxylic acid group of 3 to 6 carbon atoms,
(D) a branched or unbranched phosphonic acid group of 2 to 6 carbon atoms,
(E) a branched or unbranched sulfonic acid group of 2 to 6 carbon atoms,
(F) an amidino group of the formula

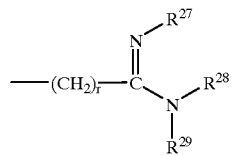

wherein r is 2, 3, 4, 5 or 6, and
$R^{27}$, $R^{28}$ and $R^{29}$ are each hydrogen atoms, or
(G) an guanidino group of the formula

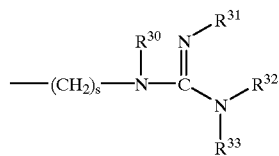

wherein s is 2, 3, 4, 5 or 6,
$R^{30}$, $R^{31}$, $R^{32}$ and $R^{33}$ are each hydrogen atoms,
$R^2$ is:
(A) a hydrogen atom, or
(B) methyl;
$R^3$ is a group of the formula —$CH_2R^{41}$, wherein
$R^{41}$ is
phenyl
wherein one or more of the hydrogen atoms of said phenyl group are necessarily and independently replaced with:
(A) $R^{62}$, which is aryl selected from the class consisting of phenyl, or pyridyl, wherein one or more of the hydrogen atoms of said aryl group may be optionally and independently replaced with:
  (i) methyl,
  (ii) a group of the formula —$COOR^{63}$, wherein $R^{63}$ is methyl,
  (iii) a group of the formula —$OR^{68}$, wherein $R^{68}$ is a hydrogen atom or methyl, or
  (iv) halogen,
(B) methyl, which may be mono- or polysubstituted with fluorine atoms or which may be monosubstituted with $R^{62}$,
(C) a group of the formula —$COOR^{73}$, wherein $R^{73}$ is methyl,
(D) a group of the formula —$COR^{78}$, wherein $R^{78}$ is methyl or $R^{62}$,
(E) a group of the formula —$CR^{79}$, wherein $R^{79}$ is a hydrogen atom, methyl or $R^{62}$,
(F) cyano,
(G) nitro, or
(H) halogen;
$R^4$ is Cl or trifluoromethyl; and,
$R^6$ is Cl or trifluoromethyl;
or a pharmaceutically acceptable salt thereof.
Even more especially preferred are compounds of the formula I
wherein:
Y is an oxygen atom;
Z is an oxygen atom;
X is a divalent group of the formula >$NR^1$,
$R^1$ is:
(A) a hydrogen atom,
(B) methyl or ethyl, or
(C) —$COCH_3$
$R^2$ is:
(A) a hydrogen atom, or
(B) methyl;
$R^3$ is a group of the formula —$CH_2R^{41}$, wherein
$R^{41}$ is
phenyl
wherein one or more of the hydrogen atoms of said phenyl group are necessarily and independently replaced with:
(A) $R^{62}$, which is aryl selected from the class consisting of phenyl, or pyridyl, wherein one or more of the hydrogen atoms of said aryl group may be optionally and independently replaced with:
  (i) methyl,
  (ii) a group of the formula —$COOR^{63}$, wherein $R^{63}$ is methyl,
  (iii) a group of the formula —$CR^{68}$, wherein $R^{68}$ is a hydrogen atom or methyl, or
  (iv) halogen,
(B) methyl, which may be mono- or polysubstituted with fluorine atoms or which may be monosubstituted with $R^{62}$,
(C) a group of the formula —$COOR^{73}$, wherein $R^{73}$ is methyl,
(D) a group of the formula —$COR^{78}$, wherein $R^{78}$ is methyl or $R^{62}$,
(E) a group of the formula —$OR^{79}$, wherein $R^{79}$ is a hydrogen atom, methyl or $R^{62}$,
(F) cyano,
(G) nitro, or
(H) halogen;
$R^4$ is Cl or trifluoromethyl; and,
$R^6$ is Cl or trifluoromethyl;
or a pharmaceutically acceptable salt thereof
Penultimately preferred are compounds of the formula I
wherein:
Y is an oxygen atom;
Z is an oxygen atom;
X is a divalent group of the formula >$NR^1$,
$R^1$ is:
(A) a hydrogen atom,
(B) methyl or ethyl, or
(C) —$COCH_3$ $R^2$ is:
(A) a hydrogen atom, or
(B) methyl;

$R^3$ is a group of the formula —$CH_2R^{41}$, wherein $R^{41}$ is phenyl wherein one or more of the hydrogen atoms of said phenyl group are necessarily and independently replaced with:
(A) $R^{62}$, which is aryl selected from the class consisting of phenyl, or pyridyl, wherein one or more of the hydrogen atoms of said aryl group may be optionally and independently replaced with:
(i) methyl, or
(ii) halogen,
(B) methyl, which may be mono- or polysubstituted with fluorine atoms,
(C) a group of the formula —$COR^{78}$, wherein $R^{78}$ is methyl or $R^{62}$,
(D) halogen;

$R^4$ is a chlorine atom; and, $R^6$ is a chlorine atom;

or a pharmaceutically acceptable salt thereof.

Ultimately preferred are the following compounds of the formula I:

1-acetyl-5-(R)-(4-bromobenzyl)-3-(2,6-dichloropyridin-4-yl)-5-methylimidazoline-2,4-dione, 5-(R)-(4-bromobenzyl)-3-(2,6-dichloropyridin-4-yl)-1-ethyl-5-methylimidazoline-2,4-dione, 5-(R)-(4-bromobenzyl)-3-(2,6-dichloropyridin-4-yl)-5-methylimidazoline-2,4-dione or a pharmaceutically acceptable salt thereof.

It will be appreciated that the compounds of the formula I have at least one chiral center. Most preferred are those compounds of formula I with the absolute stereochemistry depicted below in formula Ia.

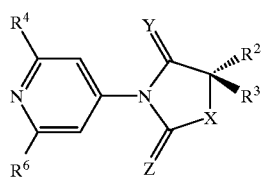

Ia

Synthesis of the Compounds of the Invention

Compounds of the invention may be prepared by the general methods described below. Typically, reaction progress may be monitored by thin layer chromatography (TLC) if desired. If desired, intermediates and products may be purified by chromatography on silica gel and/or recrystallization. Starting materials and reagents are either commercially available or may be prepared by one skilled in the art using methods described in the chemical literature.

Intermediates used in the preparation of the compounds of formula I may be prepared by the method described below and outlined in Scheme I.

Scheme I

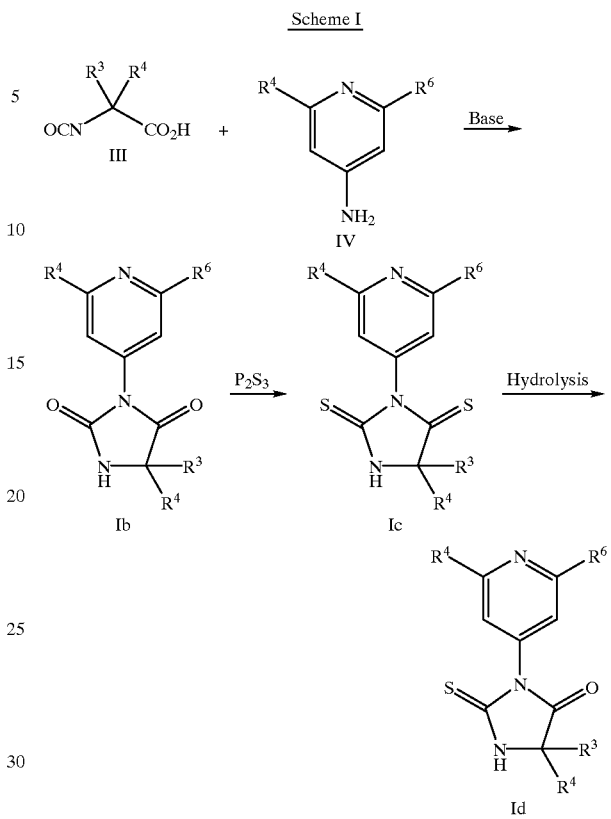

The isocyanate derivative of the appropriate amino acid (III) is reacted with the desired aminopyridine (IV) in a suitable solvent such as THF plus HMPA, in the presence of a suitable base, such as potassium bis(trimethylsilyl)amide Following workup, consisting of washing with aqueous acid, such as aqueous ammonium chloride followed by purification, for example by silica gel chromatography or recrystallization, the desired Ib is obtained.

If the thiocarbonyl is desired, several reagents are known in the literature which will convert carbonyls to thio carbonyls. A typical sequence involves heating the substrate with a reagent such as $P_2S_3$ in a high boiling solvent such as tetralin for between 1 and 48 hr. Isolation of the product follows relatively standard conditions such as the dilution of the mixture into an organic solvent such as EtOAc and washing this mixture with water and saturated aqueous NaCl followed by drying and concentration. Purification is accomplished by silica gel chromatography or recrystallization, to afford Ic.

This compound can be selectively hydrolyzed to the desired monothiocarbonyl compound depending on the choice of conditions. In general the thiocarbonyl at the 4-position of the ring is more susceptible to nucleophilic conditions. It can be converted to the 4-oxo-species (Id) by treatment with aqueous ethanolamine followed by acid hydrolysis Purification is easily performed by silica gel chromatography or recrystallization.

Alternatively, the isothiocyanate derivative of the methyl or ethyl ester of III may be reacted with IV in a suitable solvent, such as 1,4-dioxane, under an inert atmosphere at about 50–100° C. for about 1–24 hr to provide Id. If one uses the racemic III or ester of III, the product is racemic at the asymmetric carbon. By starting with a single enantiomer of III or ester of III, one obtains the single enantiomer of Id.

The starting amino acids and their derivatives necessary for the synthesis of the hydantoin and thio-hydantoin structures are either commercially available or are produced by obvious modifications of known literature procedures (see e.g.: Williams, R. W. *Synthesis of Optically Active α-Amino Acids*; Pergamon: Oxford, 1989, α-*Amino Acid Synthesis*; O'Donnell, M. J., Ed.; Tetrahedron Symposium in Print; Pergamon: London, 1988: Vol. 44, Issue 17, Jung, M. J. *Chemistry and Biochemistry of the Amino Acids*; Barrett, G. C., Ed.; Chapman and Hall: New York, 1985; p.227, and Spero, D. M.; Kapadia, S. R. J. *Org. Chem.* 1996, 61: 7398–7401). The synthesis and resolution of ethyl 2-amino-2-(4-bromobenzyl)-propanoate is given by way of example.

A solution of alanine ethyl ester hydrochloride (15.3 g, 99.3 mmol) in 60 mL of water was treated with triethylamine (14.6 mL, 104.8 mmol) at room temperature for 30 min. The mixture was then extracted twice with 100 mL of methylene chloride. The organic layers were combined, dried over sodium sulfate, and concentrated in vacuo to afford 10.0 g of the free base of the amino ester (86% yield). The residue was re-dissolved in methylene chloride and cooled in an ice bath. Magnesium sulfate (11.3 g, 93.9 mmol) was added, followed by trimethyl acetaldehyde (9.3 mL, 85.6 mmol). The ice bath was removed, and the mixture was stirred overnight. The magnesium sulfate was removed by filtration, and the filtrate was concentrated in vacuo to afford 11.8 g of the imine intermediate (74.6% yield).

The imine from above (11.8 g, 63.7 mmol) was dissolved in toluene (90 mL). 4-bromobenzyl bromide (17.5 g, 70.1 mmol) was added, and the reaction was cooled to about —10° C. Potassium tert-butoxide (8.6 g, 76.5 mmol) was added at such a rate that the temperature did not exceed 0° C. The reaction stirred in the cold bath for two hours, then was diluted with ether and washed with water (150 mL). The organic layer was dried (sodium sulfate), filtered, and concentrated in vacuo to afford a clear yellow oil. This was treated with 1N HCl (100 ml, 100 mmol) and stirred overnight. The reaction was extracted with ethyl acetate (100 mL), and the aqueous layer was to afford 14.1 g of the racemic amino ester hydrochloride (68.7% yield). Isocyanate derivatives can be made by reacting the aminoacid ester with a phosgene equivalent such as trichloromethyl chloroformate. This is exemplified in the Synthetic Examples below.

The racemic compounds can be resolved into their component enantiomers via a number of known techniques. Ethyl 2-(R)-amino-2-(4-bromobenzyl)-propanoate was produced from racemic ethyl 2-amino-2-(4-bromobenzyl)-propanoate by the following procedure: To 1.3 L of a buffer made from 13.69 g $KH_2PO_4$ and 2 L of water was added 20 g of the commercially available enzyme Lipase L10 (Amano Enzyme USA Co., Ltd, Lombardi, Ill.) followed by 12 g of the HCl salt of the racemic amino ester. The pH was monitored and 1 N KOH was added as needed to keep the pH of the mixture at 6.4. The course of the reaction was monitored with reverse phase HPLC and after 2 days, the HPLC analysis indicated that 50.4% of the starting material had been hydrolyzed. At this point enough solid $NaHCO_3$ was added to adjust the pH to 8.1 and the mixture was extracted twice with toluene, ether and EtOAc. The combined organic layers was dried and concentrated and the crude product purified by silica gel chromatography (EtOAC: Hexanes) to yield 5.21 g (87%) of ethyl 2-(R)-amino-2-(4-bromobenzyl)-propanoate. Modifications to the above procedures and further transformations of initial products to obtain additional compounds of the invention are known to those skilled in the art and are analogous to those described in WO 9839303.

SYNTHETIC EXAMPLES

Example 1

Synthesis of 5-(R)-(4-bromobenzyl)-3-(2,6-dichloropyridin-4-yl)-5-ethylimidazoline-2,4-dione Trichloromethylchloroformate (0.233 mL, 1.93 mmol) was added to a two phase mixture of 50 mL aqueous $NaHCO_3$ and 1.00 g (3.68 mmol) of (R)-α-methyl-4-bromophenylalanine methyl ester in 50 mL $CH_2Cl_2$ at 0° C. After stirring 10 min in the cold, the phases were separated and the aqueous phase was extracted 3× more with $CH_2Cl_2$. The combined organic phase was dried, concentrated in vacuo to a semisolid, re-dissolved in $CH_2Cl_2$, filtered through silica gel, and concentrated again to 0.62 g (56%) oil as the pure isocyanate.

A solution of 4.16 mL (2.08 mmol) of 0.5 M potassium bis(trimethylsilyl)amide in toluene was added to a solution of 0.34 g (2.08 mmol) 4-amino-2,6-dichloropyridine in 20 mL dry THF and 1 mL HMPA in a flame-dried flask under argon in a dry ice-alcohol bath. After stirring 5 min, a solution of the isocyanate in 5 mL THF was added dropwise over 10 min and stirred for another 0.5 hr in the cold. Aqueous $NH_4Cl$ was added which was then extracted 4× with ether, dried and concentrated in vacuo to 2.16 g oil. Flash chromatography on silica gel was performed 3 times, twice eluting with about 20% EtOAc-pet ether and finally eluting with 1% EtOAc-$CH_2Cl_2$ to give 475 mg (53%) foamy resin. (+)-Electrospray mass spec ($MH^+$ 428), consistent with the structure.

Example 2

Synthesis of 1-acetyl-5-(R)-(4-bromobenzyl)-3-(2,6-dichloropyridin-4-yl)-5-methylimidazoline-2,4-dione 4-amino-2,6-dichloropyridine (1.51 mmol) was reacted with (R)-α-methyl4-bromophenylalanine methyl ester isocyanate as described in Example 1. The reaction was quenched with 0.34 mL (3.61 mmol) acetic anhydride and stirred at room temperature overnight. Aqueous $Na_2CO_3$ was added which was extracted 4× EtOAc, dried and concentrated in vacuo to an oil. Flash chromatography on silica gel eluting with 5% acetone-petroleum ether gave 210 mg (31%) of glassy resin. Electron ionization mass spec ($M^+$ 469), consistent with the structure.

Example 3

Synthesis of 5-(R)-(4-bromobenzyl)-3-(2,6-dichloropyridin4-yl)-1-ethyl-5-methylimidazoline-2, 4-dione A solution of 1.12 mL (0.559 mmol) of 0.5 M potassium bis(trimethylsilyl)amide in toluene was added to a solution of 0.16 g (0.373 mmol) of the product of Example 1 and 0.149 mL (1.86 mmol) iodoethane in 3.5 mL dry THF+0.13 mL (0.746 mmol) HMPA. The reaction was refluxed overnight, quenched with aqueous $NH_4Cl$, extracted 4× with ether, washed 3× with $H_2O$, dried and concentrated in vacuo to an oil. Purification on Analtech 2 mm prep plates, developed in 15% acetone-petroleum ether, afforded 143 mg (84%) of sticky glassy resin. (−)-Electrospray mass spec (M+35 490) was consistent with the structure.

Description of Biological Properties

The biological properties of representative compounds of the formula I were investigated by way of the experimental protocol described below.

Assay to Determine Inhibition of LFA-1 Binding to ICAM-1

Purpose of Assay:

This assay protocol is designed to study the direct antagonism, by a test compound, of the interaction of the CAM, ICAM-1 with the Leukointegrin CD18/CD11a (LFA-1).

Description of Assay Protocol:

LFA-1 is immunopurified using the TS2/4 antibody from a 20 g pellet of human JY or SKW3 cells, utilizing a protocol previously described (Dustin, M. J.; et al., *J. Immunol.* 1992, 148, 2654–2660). The LFA-1 is purified from SKW3 lysates by immunoaffinity chromatography on TS2/4 LFA-1 mAb Sepharose and eluted at pH 11.5 in the presence of 2 mM $MgCl_2$ and 1% octylglucoside. After collection and neutralization of fractions from the TS2/4 column, samples are pooled and precleared with Protein G agarose.

A soluble form of ICAM-1 is constructed, expressed, purified and characterized as previously described (Marlin, S.; et al., *Nature*, 1990, 344, 70–72 and see Arruda, A.; et al., *Antimicrob. Agents Chemother.* 1992, 36, 1186–1192). Briefly, isoleucine 454 which is located at the putative boundary between domain 5 of the ectodomain and the transmembrane domain, is changed to a stop codon using standard oligonucleotide-directed mutagenesis. This construction yields a molecule identical with the first 453 amino acids of membrane bound ICAM-1. An expression vector is created with a hamster dihydrofolate reductase gene, a neomycin-resistance marker, and the coding region of the sICAM-1 construct described above, along with the promoter, splice signals, and polyadenylation signal of the SV40 early region. The recombinant plasmid is transfected into CHO DUX cells using standard calcium phosphate methods. Cells are passaged in selective media (G418) and colonies secreting sICAM-1 are amplified using methotrexate. sICAM-1 is purified from serum-free media using traditional non-affinity chromatographic techniques, including ion exchange and size exclusion chromatography.

LFA-1 binding to ICAM-1 is monitored by first incubating sICAM-1 at 40 $\mu$g/mL in Dulbecco's phosphate buffered saline with calcium and magnesium, additional 2 mM $MgCl_2$ and 0.1 mM PMSF (Diluting Buffer) in a 96-well plate for 30 min at room temperature. Plates are then blocked by the addition of 2% (w/v) bovine serum albumin in Diluting Buffer for 37° C. for 1 h. Blocking solution is removed from wells, and test compounds are diluted and then added followed by the addition of approximately 25 ng of immunoaffinity purified LFA-1. The LFA-1 is incubated in the presence of test compound and ICAM-1 at 37° C. for 1 h. Wells are washed 3 times with Diluting Buffer. The bound LFA-1 is detected by the addition of a polyclonal antibody directed against a peptide corresponding to the CD18 cytoplasmic tail in a 1:100 dilution with Diluting Buffer and 1% BSA and allowed to incubate for 45 min at 37° C. Wells are washed 3 times with Diluting Buffer and the bound polyclonal antibody is detected by the addition of a 1:4000 dilution of horse radish peroxidase conjugated to goat immunoglobulin directed against rabbit immunoglobulin. This reagent is allowed to incubate for 20 min at 37° C., wells are washed as above and the substrate for the horse radish peroxidase is added to each well to develop a quantitative colorimetric signal proportional to the amount of LFA-1 bound to sICAM-1. Soluble ICAM-1 (60 $\mu$g/mL) is used as a positive control for inhibition of the LFA-1/ICAM-1 interaction. The lack of the addition of LFA-1 to the binding assay is used as a background control for all samples. A dose-response curve is obtained for all test compounds.

All compounds made in the above examples were tested in this assay and each found to have a $K_d$<10 $\mu$M.

Description of Therapeutic Use

The novel small molecules of formula I provided by the invention inhibit the ICAM-1/LFA-1 dependent homotypic aggregation of human lymphocytes and human lymphocyte adherence to ICAM-1. These compounds have therapeutic utility in the modulation of immune cell activation/proliferation, e.g., as competitive inhibitors of intercellular ligand/receptor binding reactions involving CAMs and Leukointegrins. To be more specific, the compounds of the invention may be used to treat certain inflammatory conditions, including conditions resulting from a response of the non-specific immune system in a mammal (e.g., adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction or use with thrombolysis agents, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome) and conditions resulting from a response of the specific immune system in a mammal (e.g., psoriasis, organ/tissue transplant rejection, graft vs. host reactions and autoimmune diseases including Raynaud's syndrome, autoimmune thyroiditis, dermatitis, multiple sclerosis, rheumatoid arthritis, insulin-dependent diabetes mellitus, uveitis, inflammatory bowel disease including Crohn's disease and ulcerative colitis, and systemic lupus erythematosus). The compounds of the invention may also be used in treating asthma or as an adjunct to minimize toxicity with cytokine therapy in the treatment of cancers. In general these compounds may be employed in the treatment of those diseases currently treatable through steroid therapy.

Thus, another aspect of the invention is the provision of a method for the treatment or prophylaxis of the above-described conditions through the adminstration of therapeutic or prophylactic amounts of one or more compounds of the formula I.

In accordance with the method provided by the invention, the novel compounds of formula I may be administered for either a "prophylactic" or "therapeutic" purpose either alone or with other immunosuppressive or antiinflammatory agents. When provided prophylactically, the immunosuppressive compound(s) are provided in advance of any inflammatory response or symptom (for example, prior to, at, or shortly after the time of an organ or tissue transplant but in advance of any symptoms of organ rejection). The prophylactic administration of a compound of the formula I serves to prevent or attenuate any subsequent inflammatory response (such as, for example, rejection of a transplanted organ or tissue, etc.). The therapeutic administration of a compound of the formula I serves to attenuate any actual inflammation (such as, for example, the rejection of a transplanted organ or tissue). Thus, in accordance with the invention, a compound of the formula I can be administered either prior to the onset of inflammation (so as to suppress an anticipated inflammation) or after the initiation of inflammation.

The novel compounds of the formula I may, in accordance with the invention, be administered in single or divided doses by the oral, parenteral or topical routes. A suitable oral dosage for a compound of formula I would be in the range of about 0.1 mg to 10 g per day. In parenteral formulations, a suitable dosage unit may contain from 0.1 to 250 mg of said compounds, whereas for topical administration, formulations containing 0.01 to 1% active ingredient are preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula I can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenyl-ethyl alcohol.

Additionally, the compounds provided by the invention can be administered by suppository.

Formulations

Compounds of the formula I can be formulated for therapeutic administration in a number of ways. Descriptions of several exemplary formulations are given below.

Example A

| Capsules or Tablets | | | |
|---|---|---|---|
| Example A-1 | | Example A-2 | |
| Ingredients | Quantity | Ingredients | Quantity |
| Compound of formula I | 250 mg | Compound of formula I | 50 mg |
| Starch | 160 mg | Dicalcium Phosphate | 160 mg |
| Microcrys. Cellulose | 90 mg | Microcrys. Cellulose | 90 mg |
| Sodium Starch Glycolate | 10 mg | Stearic acid | 5 mg |
| Magnesium Stearate | 2 mg | Sodium Starch Glycolate | 10 mg |
| Fumed colloidal silica | 1 mg | Fumed colloidal silica | 1 mg |

The compound of formula I is blended into a powder mixture with the premixed excipient materials as identified above with the exception of the lubricant. The lubricant is then blended in and the resulting blend compressed into tablets or filled into hard gelatin capsules.

Example B

| Parenteral Solutions | |
|---|---|
| Ingredients | Quantity |
| Compound of formula I | 500 mg |
| PEG 400 | 40% by volume |
| Ethyl Alcohol | 5% by volume |
| Saline | 55% by volume |

The excipient materials are mixed and then added to one of the compounds of formula I in such volume as is necessary for dissolution. Mixing is continued until the solution is clear. The solution then filtered into the appropriate vials or ampoules and sterilized by autoclaving.

Example C

| Suspension | |
|---|---|
| Ingredients | Quantity |
| Compound of formula I | 100 mg |
| Citric acid | 1.92 g |
| Benzalkonium chloride | 0.025% by weight |
| EDTA | 0.1% by weight |
| Polyvinylalcohol | 10% by weight |
| Water | q.s. to 100 mL |

The excipient materials are mixed with the water and thereafter one of the compounds of formula I is added and mixing is continued until the suspension is homogeneous. The suspension is then transferred into the appropriate vials or ampoules.

What is claimed is:

1. A compound of the formula I

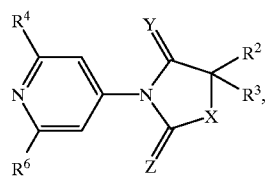

(I)

wherein:
Y is an oxygen atom;
Z is an oxygen atom;
X is a divalent group of the formula >NR$^1$,
R$^1$ is:
 (A) a hydrogen atom,
 (B) methyl or ethyl, or
 (C) —COCH$_3$
R$^2$ is:
 (A) a hydrogen atom, or
 (B) methyl;
R$^3$ is a group of the formula —CH$_2$R$^{41}$, wherein
R$^{41}$ is
 phenyl
 wherein one or more of the hydrogen atoms of said phenyl group are
  necessarily and independently replaced with:
 (A) R$^{62}$, which is aryl selected from the class consisting of phenyl, or pyridyl, wherein one or more of the hydrogen atoms of said aryl group may be optionally and independently replaced with:
  (i) methyl,
  (ii) a group of the formula —COOR$^{63}$, wherein R$^{63}$ is methyl,
  (iii) a group of the formula —OR$^{68}$, wherein R$^{68}$ is a hydrogen atom or methyl, or
  (iv) halogen,
 (B) methyl, which may be mono- or polysubstituted with fluorine atoms or which may be monosubstituted with R$^{62}$,
 (C) a group of the formula —COOR$^{73}$, wherein R$^{73}$ is methyl,
 (D) a group of the formula —COR$^{78}$, wherein R$^{78}$ is methyl or R$^{62}$,
 (E) a group of the formula —OR$^{79}$, wherein R$^{79}$ is a hydrogen atom, methyl or R$^{62}$,
 (F) cyano,
 (G) nitro, or
 (H) halogen;
R$^4$ is Cl or trifluoromethyl; and,
R$^6$ is Cl or trifluoromethyl;
or a pharmaceutically acceptable salt thereof.

2. A compound of the formula I, as claimed in claim 1, wherein:
Y is an oxygen atom;
Z is an oxygen atom;
X is a divalent group of the formula >NR$^1$, R$^1$ is:
 (A) a hydrogen atom,
 (B) methyl or ethyl, or
 (C) —COCH$_3$
R$^2$ is:
 (A) a hydrogen atom, or
 (B) methyl;
R$^3$ is a group of the formula —CH$_2$R$^{41}$, wherein
R$^{41}$ is
 phenyl
 wherein one or more of the hydrogen atoms of said phenyl group are necessarily and independently replaced with:
 (A) R$^{62}$, which is aryl selected from the class consisting of phenyl, or pyridyl,
  wherein one or more of the hydrogen atoms of said aryl group may be optionally and independently replaced with:
  (i) methyl, or
  (ii) halogen,
 (B) methyl, which may be mono- or polysubstituted with fluorine atoms,
 (C) a group of the formula —COR$^{78}$, wherein R$^{78}$ is methyl or R$^{62}$,
 (D) halogen;
R$^4$ is a chlorine atom; and,
R$^6$ is a chlorine atom;
or a pharmaceutically acceptable salt thereof.

3. A compound selected from the group consisting of:
1-acetyl-5-(R)-(4-bromobenzyl)-3-(2,6-dichloropyridin-4-yl)-5-methylimidazoline-2,4-dione;
5-(R)-(4-bromobenzyl)-3-(2,6-dichloropyridin-4-yl)-1-ethyl-5-methylimidazoline-2,4-dione; and,
5-(R)-(4-bromobenzyl)-3-(2,6-dichloropyridin-4-yl)-5-methylimidazoline-2,4-dione;
or a pharmaceutically acceptable salt thereof.

4. A compound of the formula I, as claimed in claim 1 or 2, having the absolute stereochemistry depicted below in formula Ia.

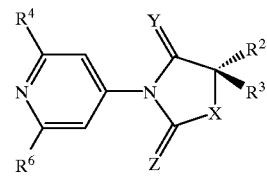

(Ia)

5. A method for the treatment of an inflammatory disease which comprises administering to a host in need or such treatment a therapeutic amount of a compound of the formula I, as claimed in claim 1, 2, 3.

6. A pharmaceutical composition comprising a compound of the formula I, as claimed in claim 1, 2, 3.

* * * * *